United States Patent
Hibino et al.

(10) Patent No.: US 8,052,325 B2
(45) Date of Patent: Nov. 8, 2011

(54) X-RAY FLUOROSCOPE TABLE AND X-RAY FLUOROSCOPE SYSTEM

(75) Inventors: Atsushi Hibino, Tokyo (JP); Tetsuji Sairaiji, Tokyo (JP); Akio Hara, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 0 days.

(21) Appl. No.: 12/517,824

(22) PCT Filed: Nov. 27, 2007

(86) PCT No.: PCT/JP2007/072798
§ 371 (c)(1),
(2), (4) Date: Jun. 5, 2009

(87) PCT Pub. No.: WO2008/069039
PCT Pub. Date: Jun. 12, 2008

(65) Prior Publication Data
US 2010/0296626 A1 Nov. 25, 2010

(30) Foreign Application Priority Data
Dec. 5, 2006 (JP) .................. 2006-328726

(51) Int. Cl.
*G01N 23/223* (2006.01)
(52) U.S. Cl. ..................... 378/197; 378/208
(58) Field of Classification Search .......... 378/37, 378/195–197, 208–209
See application file for complete search history.

(56) References Cited

U.S. PATENT DOCUMENTS
2,823,316 A 2/1958 Reynolds
3,715,587 A 2/1973 Burkhalter et al.
3,838,287 A * 9/1974 Barrett et al. ................ 378/26
3,991,317 A * 11/1976 Kunne et al. ................ 378/173
5,048,069 A 9/1991 Siczek
5,231,653 A 7/1993 Pfeiler et al.
(Continued)

FOREIGN PATENT DOCUMENTS
CN 1278357 A 12/2000
(Continued)

OTHER PUBLICATIONS
Supplemental European Search Report dated Feb. 12, 2010, issued in corresponding European Patent Application No. 07832523.
(Continued)

*Primary Examiner* — Hoon Song
(74) *Attorney, Agent, or Firm* — Antonelli, Terry, Stout & Kraus, LLP.

(57) ABSTRACT

An X-ray fluoroscope table and an X-ray fluoroscope system using this fluoroscope table with simple structure and easily ensuring an area where a person stands near the top board.

An X-ray fluoroscope table (1) comprises a stand unit (10), a support arm unit (20), a support frame (30), a top board (40), an X-ray generator (60), a column unit (50), and an X-ray detector (FPD 70).

The end of the column unit (50) on the support frame side (30) and the end on the X-ray generator (60) side are displaced from each other in the length direction of the support frame (30).

With this constitution, the area where an operator (OP3) stands can be ensured near the column unit (50).

An X-ray fluoroscope system is constituted of this fluoroscope table (1), a high-voltage generator for supplying electric power to the fluoroscope table (1), and a remote control console for integrally controlling them.

9 Claims, 19 Drawing Sheets

U.S. PATENT DOCUMENTS

| | | | |
|---|---|---|---|
| 6,412,978 B1 | 7/2002 | Watanabe | |
| 2005/0129172 A1* | 6/2005 | Mertelmeier | ............... 378/37 |

FOREIGN PATENT DOCUMENTS

| | | |
|---|---|---|
| DE | 199 27 480 A1 | 1/2001 |
| EP | 0 165 157 A1 | 12/1985 |
| JP | 06-007331 | 1/1994 |
| JP | 07-100131 | 4/1995 |
| JP | 10-248839 | 9/1998 |
| JP | 2002-017713 | 1/2002 |
| JP | 2003-334186 | 11/2003 |
| JP | 2004-033421 | 2/2004 |
| JP | 2004-160263 | 6/2004 |
| WO | WO 88/08277 A1 | 11/1988 |
| WO | WO 99/23670 A1 | 5/1999 |
| WO | WO 00/24234 A1 | 4/2000 |

OTHER PUBLICATIONS

Chinese Office Action, dated Jun. 12, 2010, issued in corresponding Chinese Patent Application No. 200780045152.

* cited by examiner

FIG.11
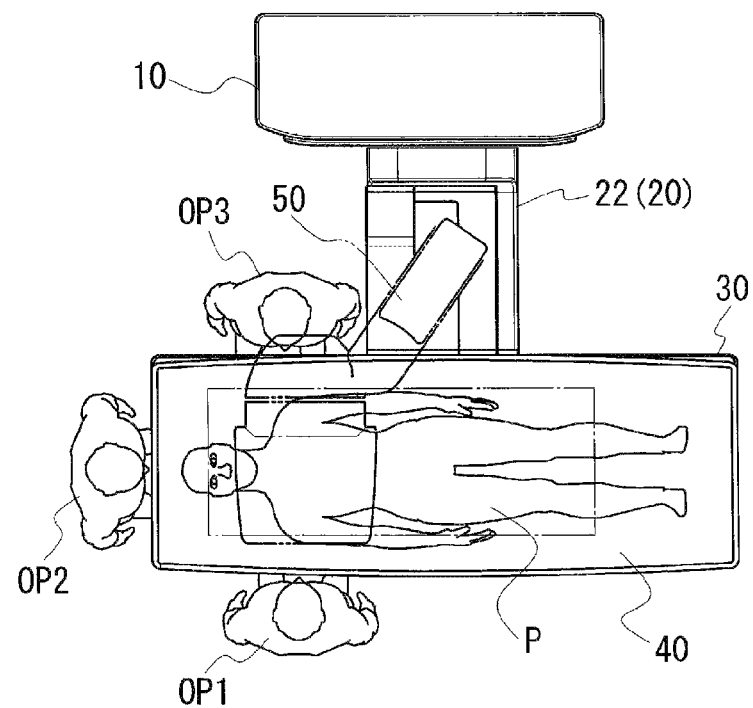
(A)
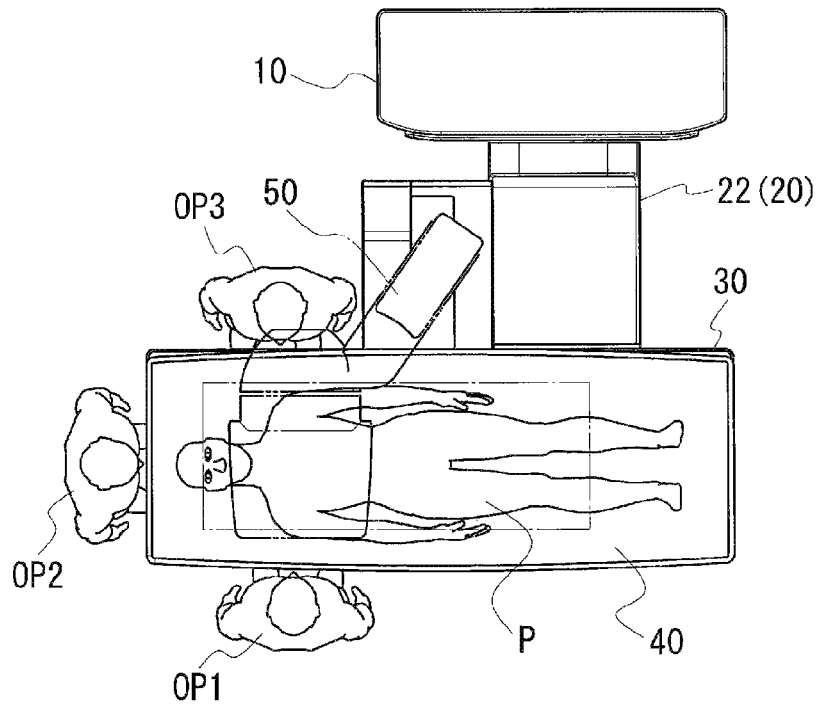
(B)

FIG.12
(A)
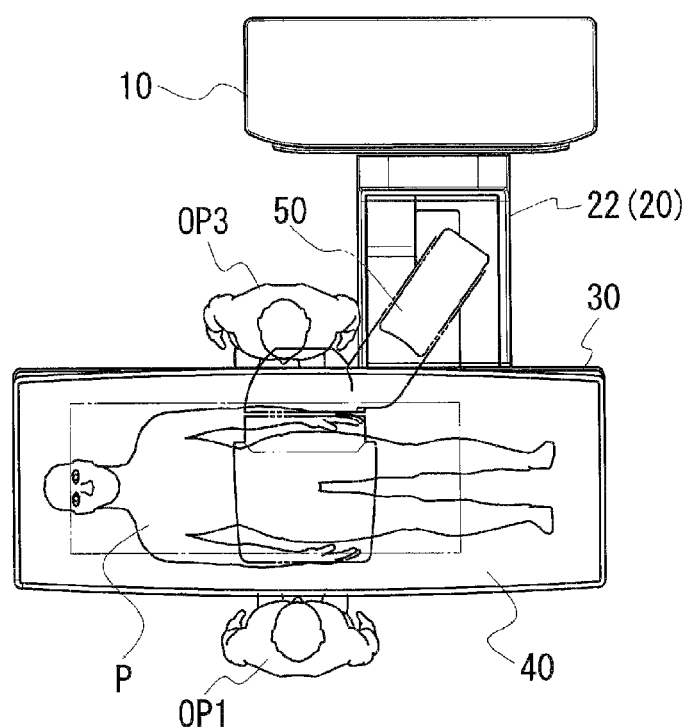
(B)
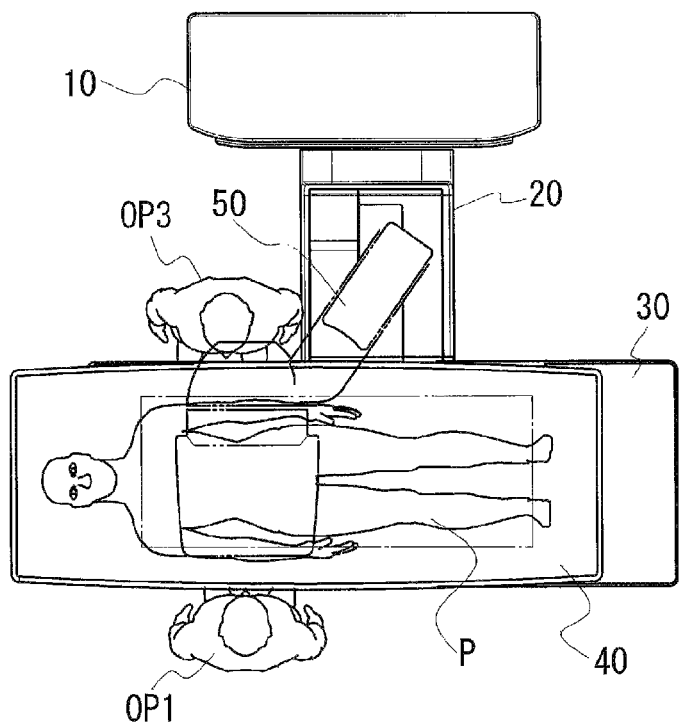

X-RAY FLUOROSCOPE TABLE AND X-RAY FLUOROSCOPE SYSTEM

TECHNICAL FIELD

The present invention relates to an X-ray fluoroscope table for carrying out fluoroscope imaging of an object to be examined, more particularly to an X-ray fluoroscope table adequate for interventional radiology (IVR).

BACKGROUND ART

In recent years, the IVR procedures which carry out treatment while performing X-ray fluoroscope simultaneously has been widely performed. In the IVR, there are cases that a plurality of people such as doctors, nurses and operators need to be involved with the treatment, as well as various pieces of equipment such as an endoscope, monitors and ultrasonic diagnostic apparatus are required to be installed around an object. Therefore, it is crucial to ensure the standing position of the operators around the object or the installation space for various pieces of equipment.

In the IVR, the X-ray fluoroscope table having a top board to which the object is placed has been often used. This kind of fluoroscope table is disclosed in Patent Document 1. This fluoroscope table has a support frame to be fixed to a floor, a top board on which the object is placed and disposed on the support frame, an X-ray generator for irradiating X-rays to the object, and an X-ray detector for detecting the X-rays which have permeated the object. The X-ray generator is disposed at the end of a column unit supported by the support frame. The X-ray detector is placed opposite from the X-ray generator in the support frame. By moving this column unit in the longitudinal direction of the support frame (body-axis direction of the object), the position of the X-ray generator with respect to the object can be variable.

At the same time, there is also a suspended-type X-ray fluoroscope table which is disclosed in Patent Document 2. This table also has a top board on which the object is placed, an X-ray generator for irradiating X-rays to the object, and an X-ray detector for detecting the X-rays which have permeated the object. In this regard, however, the X-ray generator is structured as a suspended type.

Patent Document 1: JP-A-H10-248839
Patent Document 2: JP-A-2004-160263

DISCLOSURE OF THE INVENTION

The Problem to be Solved

However in recent years, due to development of the IVR, access from three directions of the head-side of the object, right and left side of the object has been demanded, which the fluoroscope related to the Patent Document 1 could not address the need. In concrete terms, as is apparent from FIG. 7 in Patent Document 1, the column of this fluoroscope table is extended in a vertical direction from the support frame, and an arm which is further extended from the column in the direction orthogonal to the longitudinal direction of the support frame supports the X-ray generator. Therefore, the access to the object is limited to the two directions from among the head side, right side and left side of the object. Furthermore, in the case of imaging the abdominal area of the object, since the distance from the head side to the abdominal area of the object is long, the access could be practically provided only from one side of the object's body.

On the other hand, while the apparatus related to the Patent Document 2 can easily ensure the standing position for the operators around a top board, since the X-ray generator is movably suspended from the ceiling in the X-Y direction, there is a need for installing an adequately large size of an overhead traveling rail. As a result, if the ceiling in the installation space of the X-ray apparatus is low, there are cases that a suspended-type X-ray apparatus cannot be installed. Also, when the configuration for suspending a C-arm from the ceiling is used, there is a need for installation space of the apparatus itself for rotating the C-arm centering around the base for suspending the C-arm from the ceiling.

The present invention paid attention to the above-mentioned problems, and one of the objectives is to provide an X-ray fluoroscope table and the X-ray fluoroscope system using the table with simple structure capable of easily ensuring a standing position for the operators around the top board.

Means to Solve the Problem

The X-ray fluoroscope table of the present invention comprises:
a stand unit to be installed on a floor;
a support arm unit which is supported by the stand portion and is protruded toward one of the side surfaces of the stand unit;
a support frame which is supported by the support arm unit and is extended in the direction approximately orthogonal to the protruding direction of the support arm unit; and
a top board supported by the support frame, for placing an object to be examined,
characterized in further comprising:
an X-ray generator for irradiating X-rays to the object;
a column unit supported by the support frame, for supporting the X-ray generator; and
an X-ray detector which is placed opposite from the X-ray generator inside of the support frame, for detecting the X-rays which have permeated the object,
wherein the end portion on the support frame side of the column unit and is displaced with respect to the end portion on the X-ray generator side of the column unit in the longitudinal direction of the support frame.

In accordance with the X-ray fluoroscope table of the present invention, it is possible to ensure the standing position on both sides of the support frame having the X-ray generator therebetween, since the end portion on the support frame side of the column unit is displaced with respect to the end portion on the X-ray generator side of the column unit in the longitudinal direction of the support frame.

The X-ray fluoroscope table related to the present invention will be described in detail below.

The shape of the column unit does not have to be particularly limited as long as the end portion on the support frame side thereof is displaced with respect to the end portion on the X-ray generator side so as to ensure the above-described standing positions. For example, the column unit, after being arched out into the width direction of the support frame, may be extended in the longitudinal direction of the support frame, or extended in the oblique direction of the support frame (direction between the width direction and the longitudinal direction of the support frame).

In the former case, for example, the column unit is configured by a main column extended from the support frame in a vertical direction, a first arm unit extended from the end portion of the main column in the width direction of the support frame, and a second arm unit extended from the end portion of the first arm unit in the longitudinal direction of the support frame so as to support the X-ray generator by its end portion. Also, the column unit may be configured by a curved column extended from the support frame in a vertical direction and in the width direction of the support frame as being extended to its end portion, and a second arm unit extended from the end portion of the curved column in the longitudinal direction of the support frame so as to support the X-ray generator by its end portion.

In the latter case, it is preferable to configure the column unit to arch out from the support frame side toward the X-ray generator side in an oblique direction. In concrete terms, the column unit is to be extended from the support frame in a vertical direction, then in the direction which is halfway between the width direction and the longitudinal direction of the support frame as being closer to its end. By such configuration, the weight of the apparatus can be reduced since the support frame and the X-ray generator can be joined together at the shortest distance from each other, and the column unit can be formed by one member.

As for the column unit which arches out in an oblique direction, it is preferable that it is arched to be convex toward the direction away from the support frame. By such configuration, not only standing positions of operators can be ensured, but also the heightwise space for the standing positions can be widely secured. As a result, it is possible to improve the workability of operators in their standing positions.

Also, in the X-ray fluoroscope of the present invention, it is preferable that it provides configuration to perform more adequate fluoroscope imaging. In concrete terms, the support frame can be configured as slidable in the longitudinal direction of the support frame with respect to the support arm unit. In other words, the support frame is configured as slidable in the longitudinal direction of the support frame with respect to the floor. By slidably configuring the support frame, as will be described in an embodiment later referring to FIG. 12, it is possible to perform fluoroscope imaging of the object while ensuring the standing positions of the operators and moving the range of X-ray irradiation in a wide range. Further, as the imaging table disclosed in Patent Document 1, the top board supported by the support frame may be configured slidably with respect to the support frame.

Hereinafter, the configuration of the units other than the column unit and the support frame in the X-ray fluoroscope table of the present invention will be described.

The stand unit of the imaging table related to the present invention is a chassis that contains units such as a control unit for controlling the respective components of the imaging table. This stand unit is disposed on the floor, for supporting the whole imaging table.

The support arm unit is supported by the stand unit so as to be protruded toward one side surface of the stand unit, for supporting the support frame. It is preferable that the support arm unit is supported by the stand unit via an axis unit so as to rotatably support the support frame. By rotatably configuring the support arm unit, the position of the object can be freely changed. Also, it is preferable that the axis unit (support arm unit) is supported as capable of being lifted and lowered with respect to the stand unit. In this manner, by configuring the support arm unit as capable of being lifted and lowered, it is easier to place the object on the top board which is disposed on the support frame, and the height of the top board can be adjusted for smoother operation.

The X-ray generator to be used for the table can be the commonly used one having an X-ray tube for generating X-rays. Also, it is preferable that the X-ray generator is swingably supported by the column unit so as to swing the irradiation direction of X-rays in the longitudinal direction of the support frame.

The X-ray detector can be the combination of an image intensifier and a TV camera, or an X-ray flat panel detector (FPD). In particular, it is preferable to use a small-sized and light-weight FPD considering that the X-ray detector is to be disposed inside of the support frame.

Also, it is desirable that the X-ray fluoroscope table has a display device for displaying the fluoroscopic images of the object. This display device may be disposed separately from the imaging table, or may be integrated with the imaging table. In the case of integrating the display device with the imaging table, they can be supported by the stand unit via a multi-joint arm. By such configuration, the display device can be disposed in the position where the IVR cannot be interfered, and the display device can be easily faced toward operators where they can observe the fluoroscopic images easily.

In the fluoroscope imaging, there are cases that the imaging is performed while pressing the object in the area of interest. Given this factor, the imaging table of the present invention may comprise a pressing tube for pressing an area of interest of the object upon imaging, and a pulling arm wherein its one end is to be coupled to the pressing tube and the other end to the column unit. Then when the area of interest in the object is pressed by the pressing tube, the pressing tube is pulled toward the area of interest by the pulling arm. When the pressing tube is not being used, at least the pulling arm may be contained in the column unit. It is needless to say that it can be configured so that the pressing tube also can be contained in the column unit. Configuring the pulling arm and the pressing tube to be contained in the column unit when the pressing tube is not in use can prevent these members from being obstruction for imaging.

The X-ray fluoroscope imaging system for performing fluoroscope imaging of an object using the above-described X-ray fluoroscope imaging table should comprise at least the following components.

I. An X-ray fluoroscope imaging table of the present invention.

II. A high-voltage generator for supplying electric power to an X-ray generator of the imaging table.

III. A remote console for integrally controlling the imaging table and the high-voltage generator.

While the arrangement of the respective components for the X-ray fluoroscope system is not particularly specified, it is preferable to install the imaging table in the imaging room and to install the remote console in a room separate from the imaging room. At this time, while the high-voltage generator can be installed in the imaging room, operation room or any of the other rooms, it is preferable to install it in the imaging room considering the wiring of the imaging table and the high-voltage generator.

Or, another X-ray technician who operates the imaging table may dispose a console to perform close operation of the imaging table in the imaging room.

Upon performing a fluoroscope imaging of an object using the X-ray fluoroscope system of the above-described present invention, the object is placed on a top board (support frame), and X-rays are irradiated from an X-ray generator. The irradiated X-rays are transmitted through the object, detected by an X-ray detector disposed in the support frame, and acquired as image data in accordance with the incoming radiation amount. The acquired image data is performed with various image processing, and displayed on a display device as perspective images. In this system, when performing the IVR, the object can be accessed by operators from both sides thereof due to the usage of the X-ray fluoroscope imaging table related to the present invention.

In accordance with the X-ray fluoroscope table and the X-ray fluoroscope system, since the end portion on the support frame side of the column unit is displaced with respect to the end portion on the X-ray generator side of the column unit in the longitudinal direction of the support frame, it is possible to ensure the standing positions on both sides of the support frame having the X-ray generator therebetween. Therefore, the operators can have access to the object from both sides of the object, whereby the IVR can be performed effectively.

BRIEF DESCRIPTION OF THE DIAGRAMS

FIG. 11 shows the state of performing fluoroscope imaging on the pectoral region of the object, wherein (A) shows the state that the support frame is not moved and (B) shows the state that the support frame is moved.

FIG. 12 shows the state of performing fluoroscope imaging on the lower abdominal region of the object, wherein (A) shows the state that the support frame is moved and (B) shows the state that a top board is moved without moving the support frame.

BEST MODE FOR CARRYING OUT THE INVENTION

Hereinafter, the X-ray fluoroscope table and the X-ray fluoroscope system using the table will be described on the basis of the attached diagrams.

Figure 1:
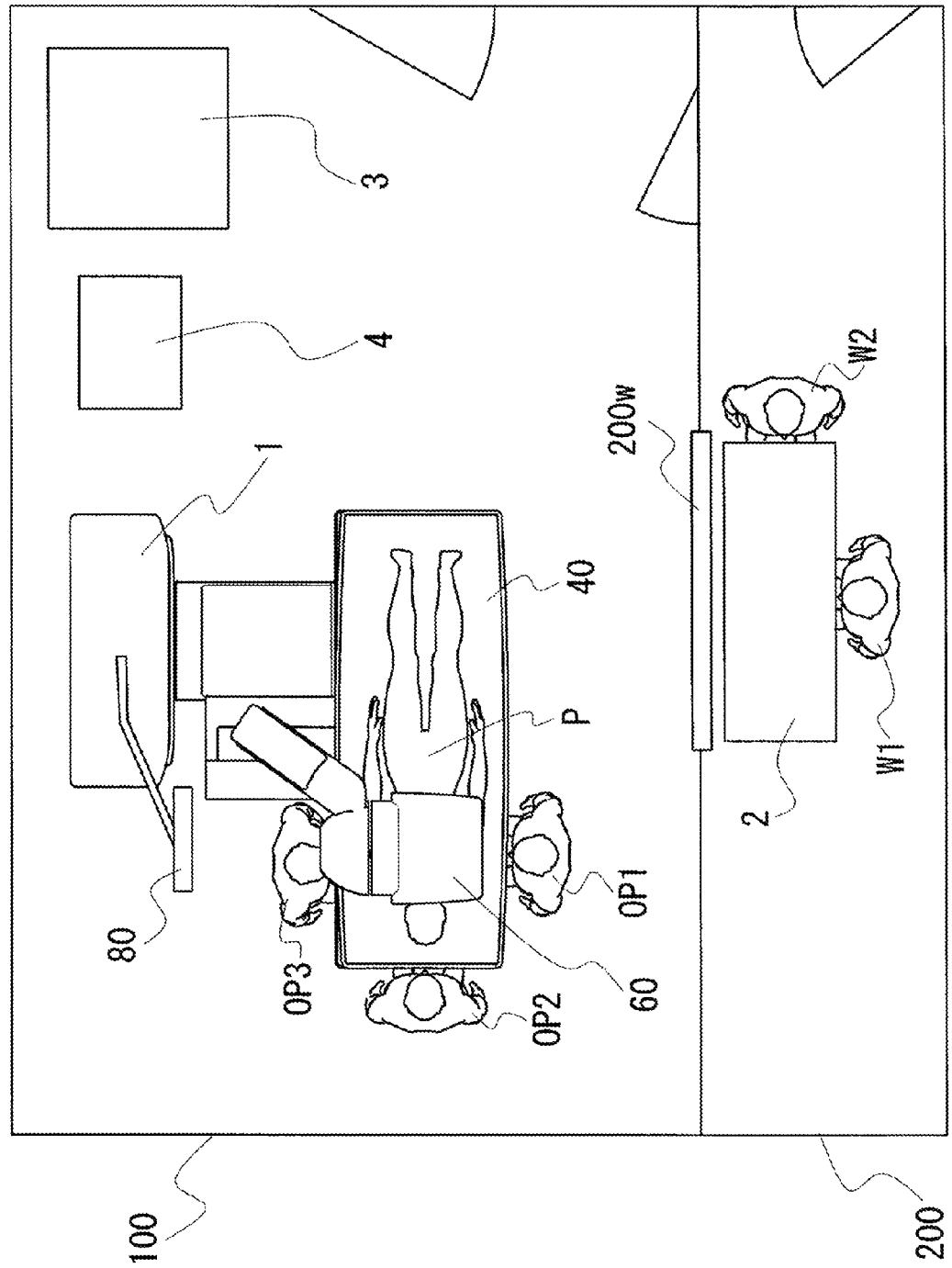
FIG. 1 is a schematic configuration diagram of the X-ray fluoroscope system illustrated in an embodiment.

As shown in FIG. 1, the X-ray fluoroscope system of the present invention comprises:
X-ray fluoroscope table 1;
high-voltage generator 3 for supplying electric power to the fluoroscope table;
wave-tail interrupting device 4 for cutting a wave tail of an electricity waveform provided from the high-voltage generator 3; and
remote console 2 for integrally controlling the above-mentioned devices. From among the devices by which the system is formed, the X-ray fluoroscope table 1, high-voltage generator 3 and wave-tail interrupting device 4 are disposed in imaging room 100 in which fluoroscope imaging is to be performed on object P, and the remote console 2 is disposed in operation room 200 which is adjacent to the imaging room 100. The operation room 200 is configured so as to defilade X-rays generated in the imaging room 100, which prevents X-ray technicians W1 and W2 who operate the imaging table 1 from being exposed to radiation. Between the imaging room 100 and the operation room 200, window 200w is provided so that the condition in the imaging room 100 can be monitored from the operation room 200. This window 200w is also formed by lead-containing glass, etc. to defilade X-rays from the imaging room 100.

When the IVR which is for performing a medical treatment while performing a fluoroscope imaging of the object P at the same time using the above-mentioned system, the object P is to be laid on the top board 40 of the imaging table 1, and operators OP1~OP3 are placed around the object P. Then in accordance with the procedure of the IVR, the X-ray technicians W1 and W2 operate the remote console 2 and adjust the intensity, etc. of the X-rays to be irradiated to the object P. On the basis of the intensity and irradiation intervals of the X-rays inputted to the remote console 2, the high-voltage generator 3 supplies the tube current having pulse waveforms to the imaging table (X-ray generator 60) intermittently. The imaging table 1 irradiates X-rays intermittently to the object P in accordance with the tube current, and continuously displays the fluoroscopic images of the object P corresponding to each X-ray on the display device 80. Upon providing tube current to the imaging table 1, by cutting the wave tails of the tube current having pulse waveforms by the wave tale interrupting device 4, it is possible to perform a stable fluoroscope imaging.

[General Configuration of the X-ray Fluoroscope Table]

As shown in FIGS. 2~5, the X-ray fluoroscope table 1 comprises:

stand unit 10 to be disposed on the floor;

support arm unit 20 supported by the stand unit 10 and is protruded toward one of the side surfaces of the stand 10;

support frame 30 supported by the support arm unit 20 and is extended in the direction approximately orthogonal the protruding direction of the support arm unit 20; and top board 40 to which the object P is placed, supported by the support frame 30.

The X-ray fluoroscope table 1 also comprises:

X-ray generator 60 for irradiating X-rays to the object P;

column unit 40 supported by the support frame 30, for supporting the X-ray generator 60; and FPD (X-ray detector) 70 disposed facing the X-ray generator 60 inside of the support frame 30, for detecting the X-rays transmitted through the object P.

Further, the X-ray fluoroscope table 1 comprises monitor (display device) 80 for displaying the fluoroscopic images of the object P.

The X-ray fluoroscope table 1 can operate the respective components in the directions shown in FIG. 2 as cited below.

Direction A1 . . . the longitudinal direction of the support frame 30 with respect to the stand 10 (the direction orthogonal to the protruding direction of the support arm unit 20).

Direction A2 . . . lifting and lowering direction of the support frame 30 with respect to the stand unit 10 (the direction vertical to the floor).

Direction A3 . . . uprising/reclining direction of the support frame 30 (rotation direction centering on the protruding direction of the support arm unit).

Direction A4 . . . longitudinal direction of the column unit 50 with respect to the support frame 30 (longitudinal direction of the support frame 30).

Direction A5 . . . crosswise movement direction of the column unit 50 with respect to the support frame 30 (protruding direction of the support arm unit 20)

Direction A6 . . . rotation movement direction of the X-ray generator 60 with respect to the end portion of the column unit 50 (rotating direction centering around the A5 direction)

Direction A7 . . . longitudinal moving direction of the FPD 70 with respect to the support frame 30 (longitudinal direction of the support arm unit 20)

Direction A8 . . . crosswise movement direction of the FPD 70 with respect to the support frame 30 (protruding direction of the support arm unit 20)

Direction A9 . . . rotation movement direction of the FPD 70 (rotating direction centering around the direction vertical to the floor)

By moving the respective components of the imaging table 1 in the above-described directions A1~A9, the position of the object P placed on the top board 40 or the irradiation range of the X-rays to be irradiated to the object P can be changed. As a result, it is possible to perform fluoroscope imaging of the object P effectively and accurately.

Hereinafter, the respective components of the X-ray fluoroscope table 1 and the mechanism for operating the respective components will be described in detail. While the description below will be basically based on FIG. 2~FIG. 5, FIG. 6~FIG. 10 illustrating the condition of the imaging table 1 from which the outer covering is removed will be referred to as the need arises.

[A Stand Unit]

Figure 6:
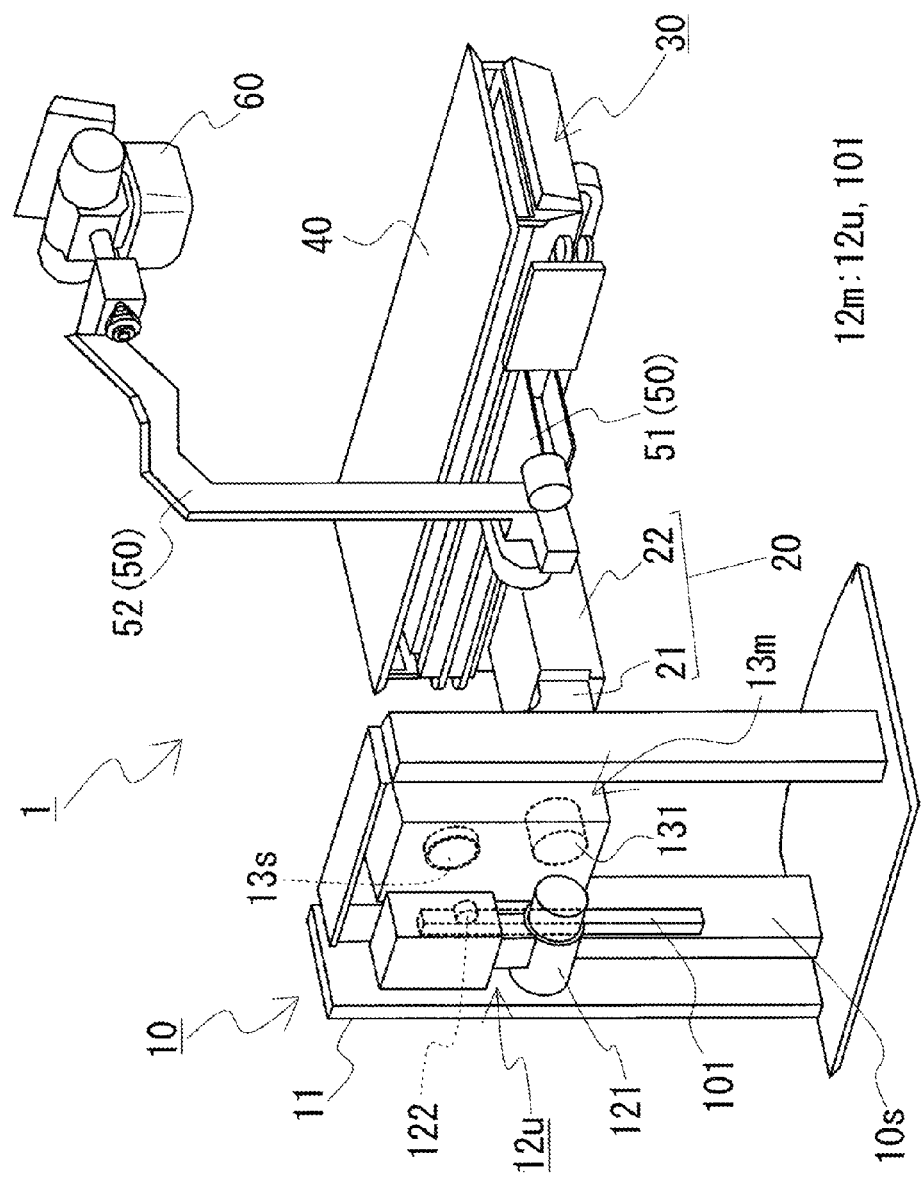
FIG. 6 is a perspective view of the X-ray fluoroscope table from which the cover for covering the respective parts of the table is removed, viewing from the opposite direction from the viewing direction in FIG. 2, for showing the mechanism to operate a support frame with respect to a stand unit.

The stand unit 10 is a chassis for supporting the whole imaging table 1. Inside of the stand unit 10, as shown in FIG. 6, units such as A2-direction lifting and lowering mechanism 12m for lifting and lowering the support arm unit 20 with respect to the stand unit 10 and A3-direction rotating mechanism 13m for rotating the support arm unit 20 with respect to the stand unit 10 are contained. Also, in side board 11 adjacent to framework 10s that supports these mechanisms, a number of control panels are mounted for controlling the respective components.

The A2-direction lifting and lowering mechanism 12m comprises lifting and lowering rack 101 to be provided on the framework 10s of the stand unit 10, and lifting and lowering unit 12u to be lifted and lowered in the up-and-down direction of the stand unit 10 along the lifting and lowering rack 101. The lifting and lowering unit 12u has motor 121 and lifting and lowering pinion 122 to be rotated by the drive of the motor 121, and the lifting and lowering unit 12u is lifted and lowered along the lifting and lowering rack 101 by the interlocking of the lifting and lowering pinion 122 and the lifting and lowering rack 101. Also, the A3-direction rotating mechanism 13m is supported by the lifting and lowering unit 12u.

The A3-direction rotating mechanism 13m has motor 131 and rotation axis unit 13s which is coupled to the support arm unit 20 to be described below. The driving force of the motor 131 is transmitted to the rotation axis unit 13s via two-tiered reduction gears. Thus the rotation axis unit 13s can be rotated using the drive of the motor 131.

[Support Arm Unit]

The support arm unit 20 has coupling piece 21 on the stand unit side and coupling piece 22 on the support frame side, and the coupling piece 21 on the stand unit side is supported by the stand unit 10 via the previously mentioned rotation axis unit 13s. That is, the support arm unit 20 is supported pivotally by the A3-direction rotating mechanism 13m of the stand unit 10 via the rotation axis unit 13s so as to be rotatable in the arrow A3-direction shown in FIG. 2. Also, since the A3-direction rotating mechanism 13m is supported by the lifting and lowering unit 12u as previously mentioned, the support arm unit 20 is configured as capable of being lifted and lowered in the arrow A2-direction shown in FIG. 2.

Figure 7:
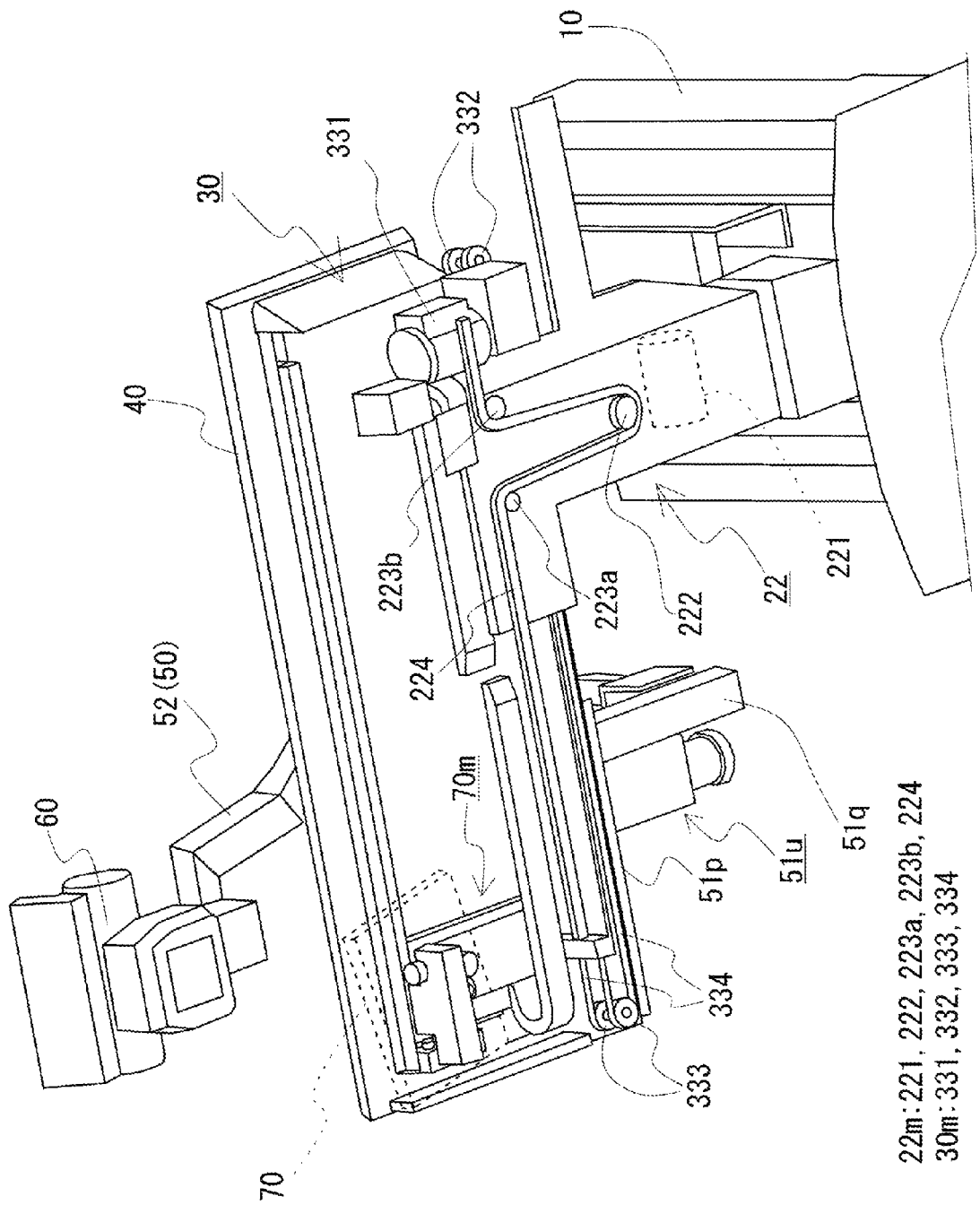
FIG. 7 is a perspective view of the X-ray fluoroscope table from which the cover for covering the respective parts of the table is removed, viewing from the bottom thereof for showing the mechanism to operate the support frame with respect to a support arm unit.

On the other hand, in the coupling piece 22 on the support frame side of the support arm unit 20, A1-direction sliding mechanism 22m is provided for sliding the support frame 30 in the longitudinal direction of the support frame 30 with respect to the support arm unit 20 (refer to FIG. 7). The A1-direction sliding mechanism 22m comprises motor 221, main sprocket wheel 222 which rotates by the drive of the motor 221, two driven sprocket wheels 223a and 223b, and chain 224 interlocked to the sprockets 222, 223a and 223b. Both ends of the chain 224 are fixed to a holding part of the support frame 30 (not shown in the diagram). Therefore, the chain 224 can be sent forth in the horizontal direction in FIG. 7 by the rotation of the main sprocket 222, whereby it is possible to slide the support frame 30 in the arrow A1-direction in FIG. 2 with respect to the support arm unit (coupling piece 22 on the support frame side).

[Support Frame]

The support frame 30 is configured slidably in the direction orthogonal to the protruding direction of the support arm unit 20 (direction A1 in FIG. 2) with respect to the support arm unit 20, by the previously described A1-direction sliding mechanism 22m. On the upper part of the support frame 30, the top board for the object P is to be placed is provided. While the top board 40 is fixed to the imaging table 1 related to the present embodiment, it can be configured slidably with respect to the support frame 30. Also, operation panels 301 and 302 are provided on the side surface of the support frame 30 which is on the opposite side of the column unit 50 and on the end surface of the bending direction side of the column unit 50 from among the end surfaces of the support frame 30 (on the left side in FIG. 2). By these operation panels 301 and 302, the corresponding respective components can be driven in the directions A1~A9 shown in FIG. 2. Also, pressing device 90 to be described later can be driven by the operation panels 301 and 302.

Inside of the support frame 30, A4-direction sliding mechanism 30m is provided for sliding the column unit 50 in the longitudinal direction of the top board 40 with respect to the support frame 30 (refer to FIG. 7). The A4-direction sliding mechanism 30m has motor 331 to be provided on one end side in the longitudinal direction of the support frame 30, main sprocket wheel 332 to be rotated by the drive of the motor 331, driven sprocket wheel 333 to be provided on the other side of the support frame 30 and chain 334 to be coupled to both sprocket wheels 332 and 333. As to be described later, basement 51 of the column unit 50 is fixed to the chain 334, and the basement 51, i.e. column unit 50 can be slid in the horizontal direction in the diagram (direction A4 in FIG. 2) by rotating the chain 334 by the sprockets 332 and 333 (refer also to FIG. 8).

Further, FPD driving mechanism 70m is provided inside of the support frame 30, which will be described later in the section of FPD.

[Column Unit]

The column unit 50 comprises the basement 51 configured slidably in the longitudinal direction of the support 30 by the A4-direction sliding mechanism 30m, main column body 52 to be fixed to the basement 51 and coupling unit 53 for supporting the X-ray generator 60 at the end of the main column body 52. The main column body 52 is extended in the vertical direction from the basement 51, and also in both longitudinal and width directions of the support frame 30 as the main column body 52 gets toward the coupling unit 53 (refer to FIGS. 4 and 5). In this manner, standing positions of the operators OP1 and OP3 can be ensured on both sides of the support frame 30 having the X-ray generator 60 therebetween, whereby the operators can have access to the object P from three directions which are the head-region side and both sides of the object P.

Figure 2:
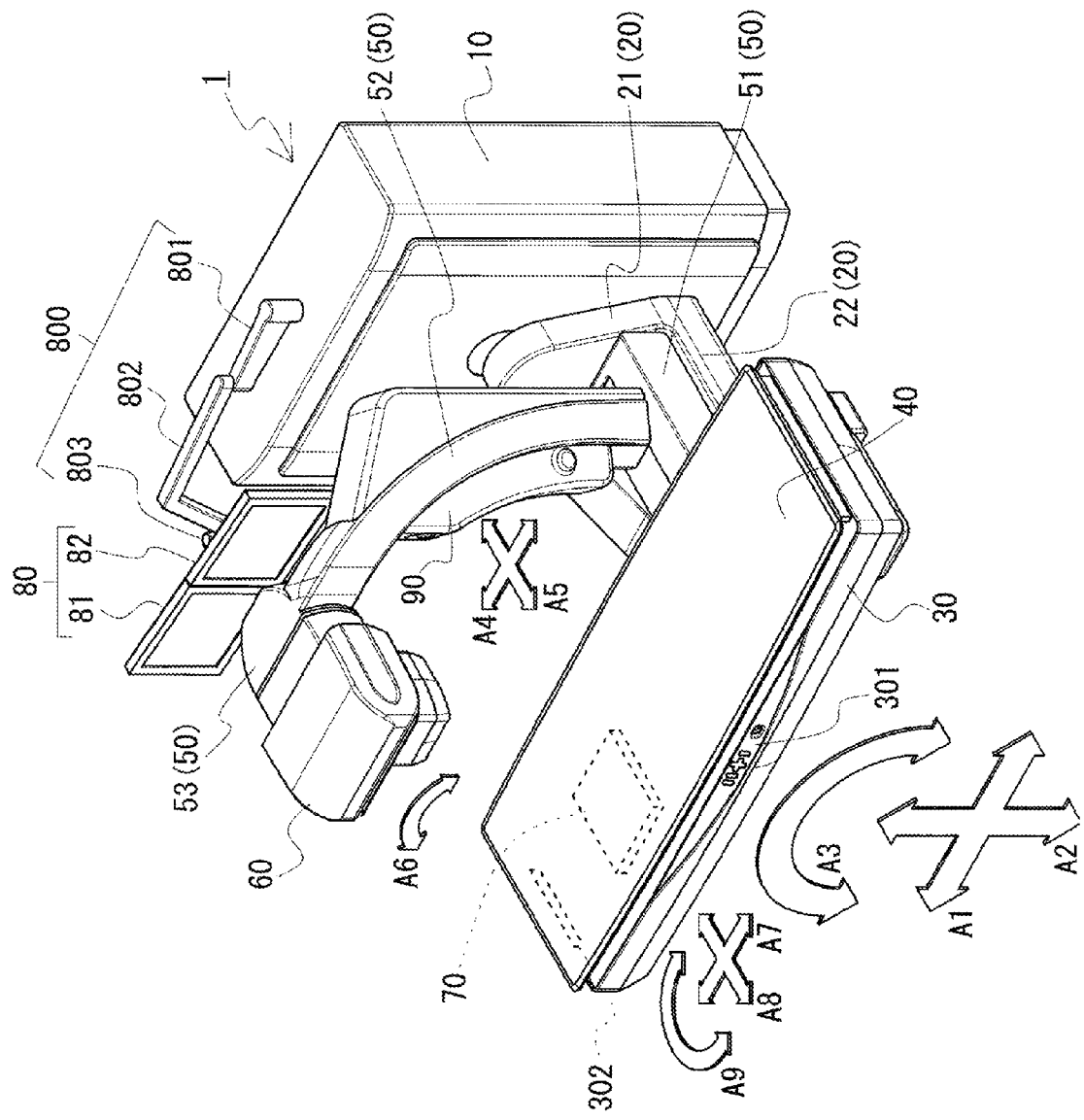
FIG. 2 is a perspective view of the X-ray fluoroscope table illustrated in the embodiment.
Figure 3:
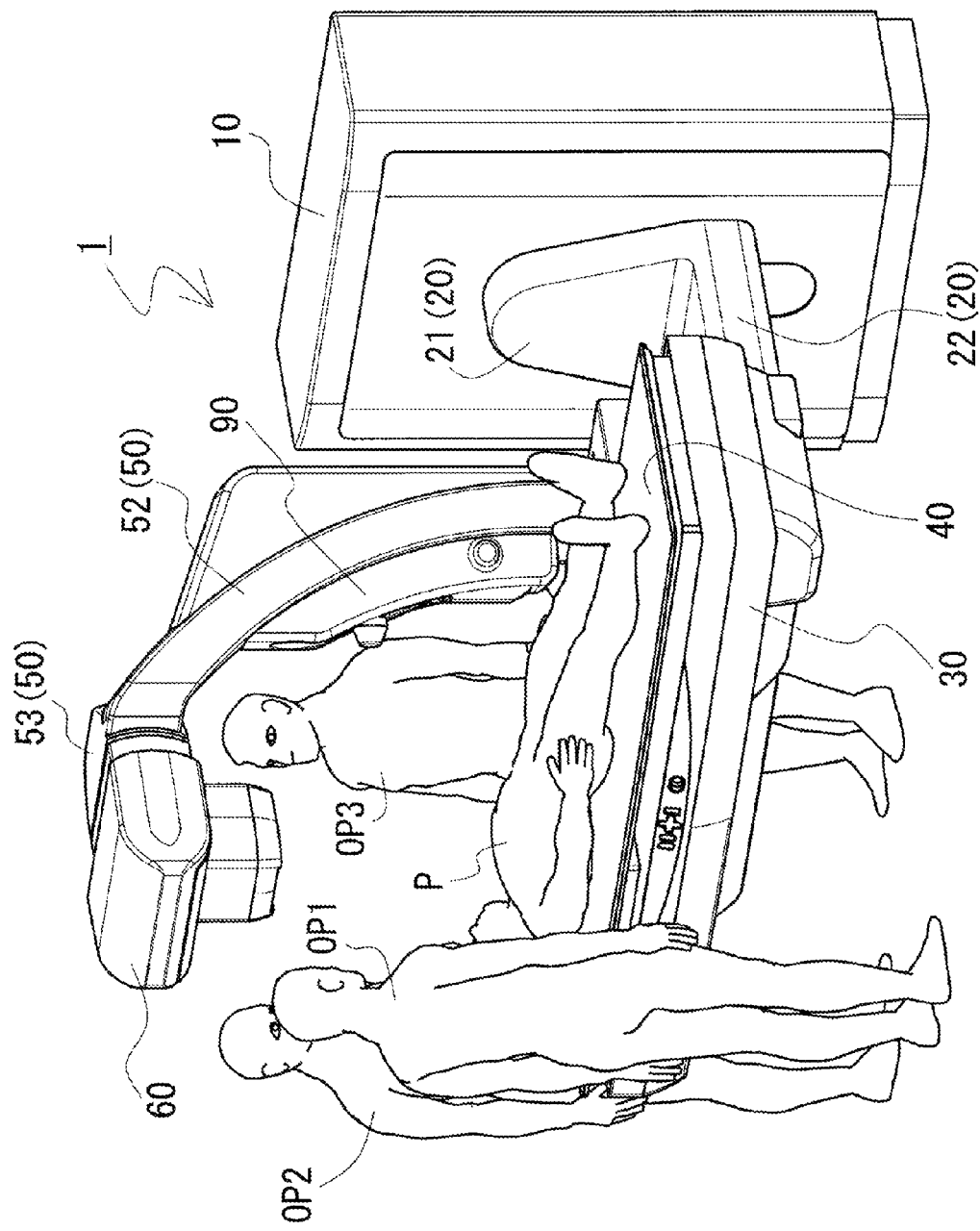
FIG. 3 is a perspective view showing the state wherein an object and operators are placed at the X-ray fluoroscope table.
Figure 4:
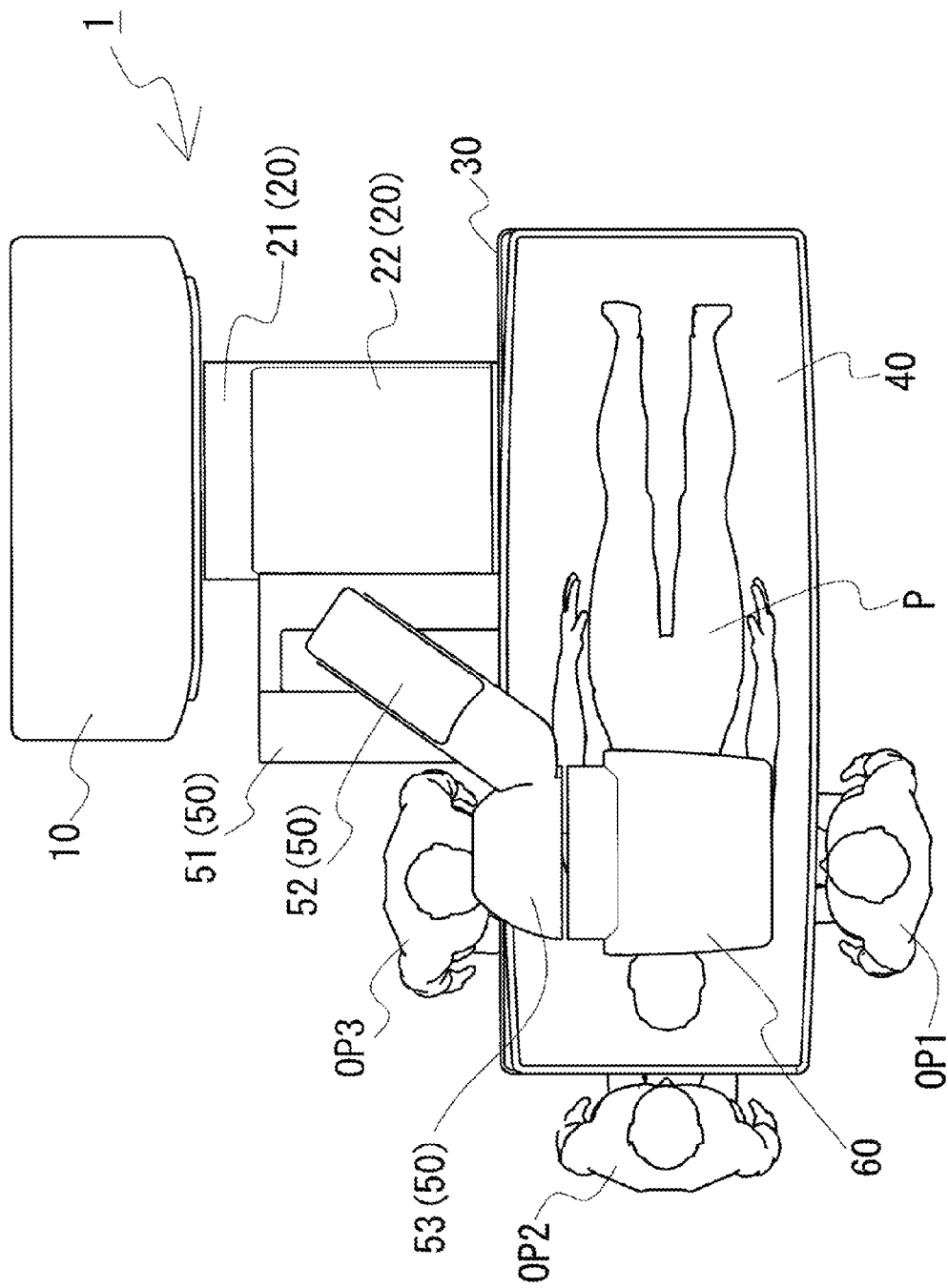
FIG. 4 is a top view illustrating the state wherein the object and the operators are placed at the X-ray fluoroscope table.

The main column body 52 of the column unit 50 is curved so as to be convex in the direction away from the support frame 30, which is to be protruded toward the standing unit 10 side (refer to FIGS. 2 and 3). Therefore, the main column body 52 does not interfere the movement of operator OP3 who stands in the vicinity of the column unit 50.

Further, pressing device 90 is provided to the main column body 52 on the side facing the support frame 30. The pressing device 90 is a device for imaging while pressing the object P in the region of interest.

Figure 8:
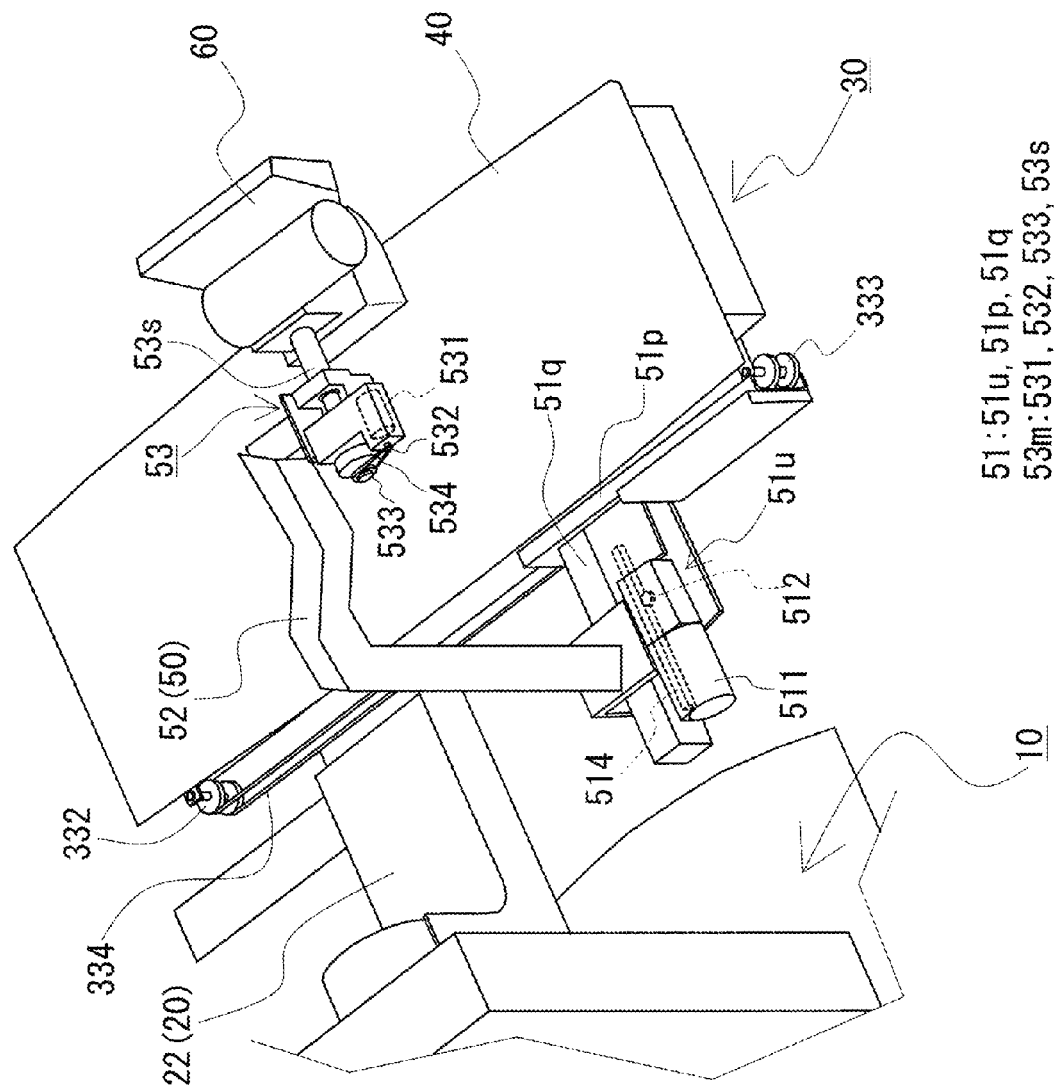
FIG. 8 is a perspective view of the X-ray fluoroscope table from which the cover for covering the respective parts of the table is removed, viewing from the top for showing the mechanism to operate the column unit with respect to a support frame.

As shown in FIG. 8, the basement 51 of the column unit 50 comprises slider piece 51p to be fixed to the chain 334 of the A4-direction sliding mechanism 30m and basement framework 51q to be extended from the slider piece 51p to the side of stand unit 10. Also, the basement 51 has A5-direction sliding unit 51u for sliding the column unit 50 in the width direction of the support frame 30 with respect to the support frame 30. The A5-direction sliding unit 51u has motor 511 and pinion 512 to be rotated by the drive of the motor, and the pinion 512 is interlocked with rack 514 provided on the basement framework 51q. In other words, the A5-direction sliding unit 51u can be slid along the rack 514 by the rotation of the pinion 512 so as to move the unit 51u in the width direction of the support frame 30 with respect to the basement framework 51q. Here, the A5 direction sliding unit 51u is coupled to the main column body 52, thus by moving the A5-direction sliding unit 51u in the width direction of the support frame 30, the whole column unit 50 can be moved in the same direction (direction A5 in FIG. 2).

Inside of the coupling unit 53 of the column unit 50, A6-direction rotating mechanism 53m is provided for rotating the X-ray generator 60 with respect to the coupling unit 53 (refer to FIG. 8). The A6-direction rotating mechanism 53m has motor 531, main pulley 532 that rotates by the rotation of the motor 531, rotation axis unit 53s wherein driven pulley 533 is provided on its end, and belt 534 for coupling the both pulleys 532 and 533. Therefore, the rotation axis unit 53s can be rotated by rotating the main pulley 532, whereby the X-ray generator 60 fixed to the opposite end from the driven pulley 533 can be rotated in the direction A6 shown in FIG. 2 with respect to the end portion of the column unit 50 (end portion of the coupling unit 53).

[X-ray Generator]

The X-ray generator 60 is attached on the end side of the column 50 for irradiating X-rays to the object P. The X-ray generator 60 may have the common configuration which has an X-ray tube for generating X-rays by receiving electric power supply from the high-voltage generator 3. Also, the X-ray generator 60 may comprise devices such as a common adjustable aperture for limiting the irradiation range of X-rays or an X-ray filter for selectively transmitting the X-rays of specified energy.

The X-ray generator 60 is configured rotatable in the arrow A6 direction in FIG. 2 by the above-described A6-direction rotating mechanism 53m, and is capable of waving the irradiation direction of X-rays in the longitudinal direction of the top board 40.

[FPD]

In FPD 70, a plurality of detection elements are two-dimensionally arrayed, so as to detect the image data in accordance with the incoming radiation amount of the X-rays irradiated from the X-ray generator 60 and transmitted through the object P. The FPD 70 is disposed inside of the support frame 30 and on top of FPD driving mechanism 70m as shown in FIG. 7, and is not mechanistically coupled to the column unit 50 which supports the X-ray generator 60. Consequently, the X-ray fluoroscope table 1 controls the FPD 70 to operate in the longitudinal direction of the support frame 30 with respect to the support frame 30 (direction A7 in FIG. 2) and the width direction of the support frame 30 (direction A8 in FIG. 2) to make it face the X-ray generator 60. More specifically, the FPD 70 is to be controlled to operate so that the optical axis of X-rays penetrates the center of the FPD 70. Control of the operation of the FPD 70 to follow the movement of the X-ray generator 60 is performed based on the sensor for detecting the sliding condition of the basement 51 of the column unit 50 with respect to the support frame 30 and the sliding condition of the main column body 52 with respect to the basement 51.

Figure 9:
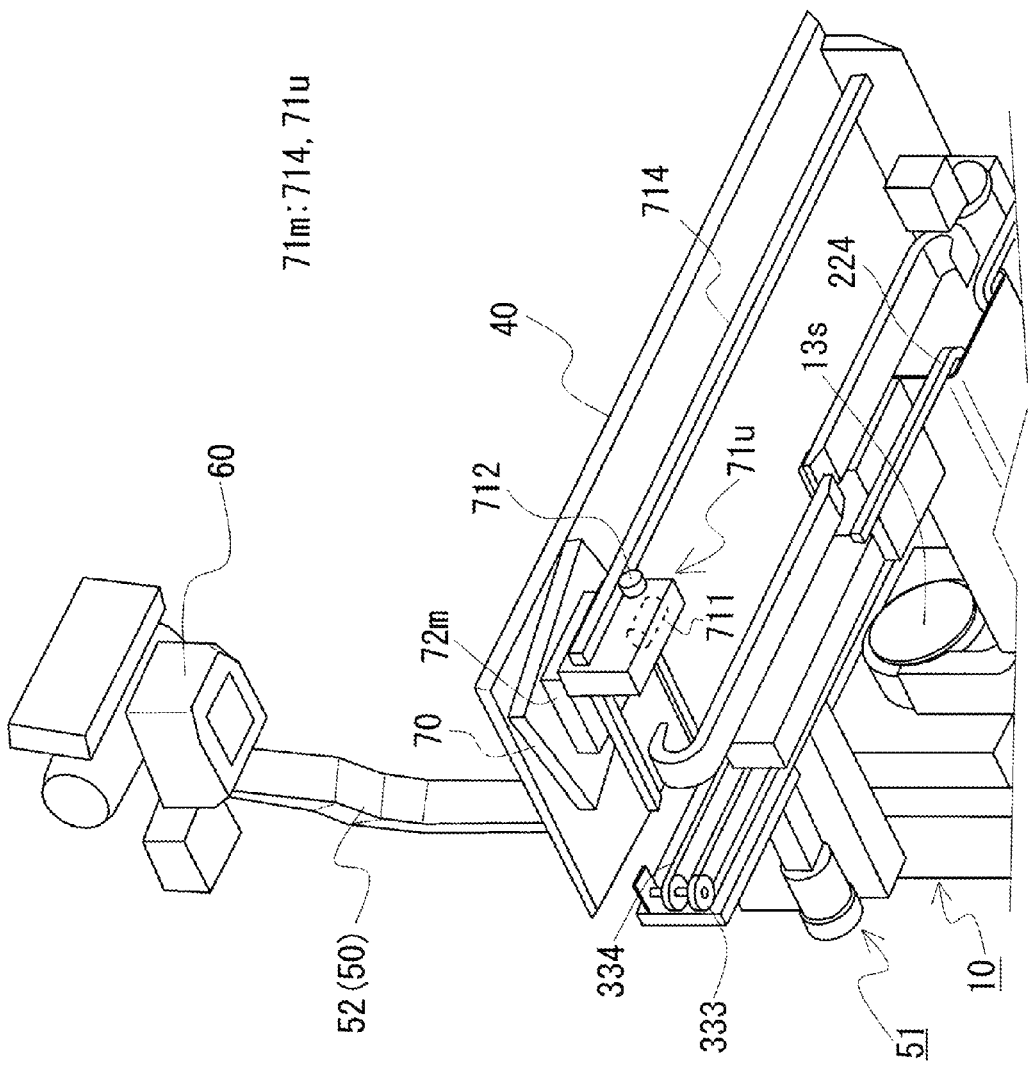
FIG. 9 is a perspective view of the X-ray fluoroscope table from which the cover for covering the respective parts of the table is removed, viewing from the bottom thereof for showing the mechanism to operate an FPD in the longitudinal direction of the support frame.
Figure 10:
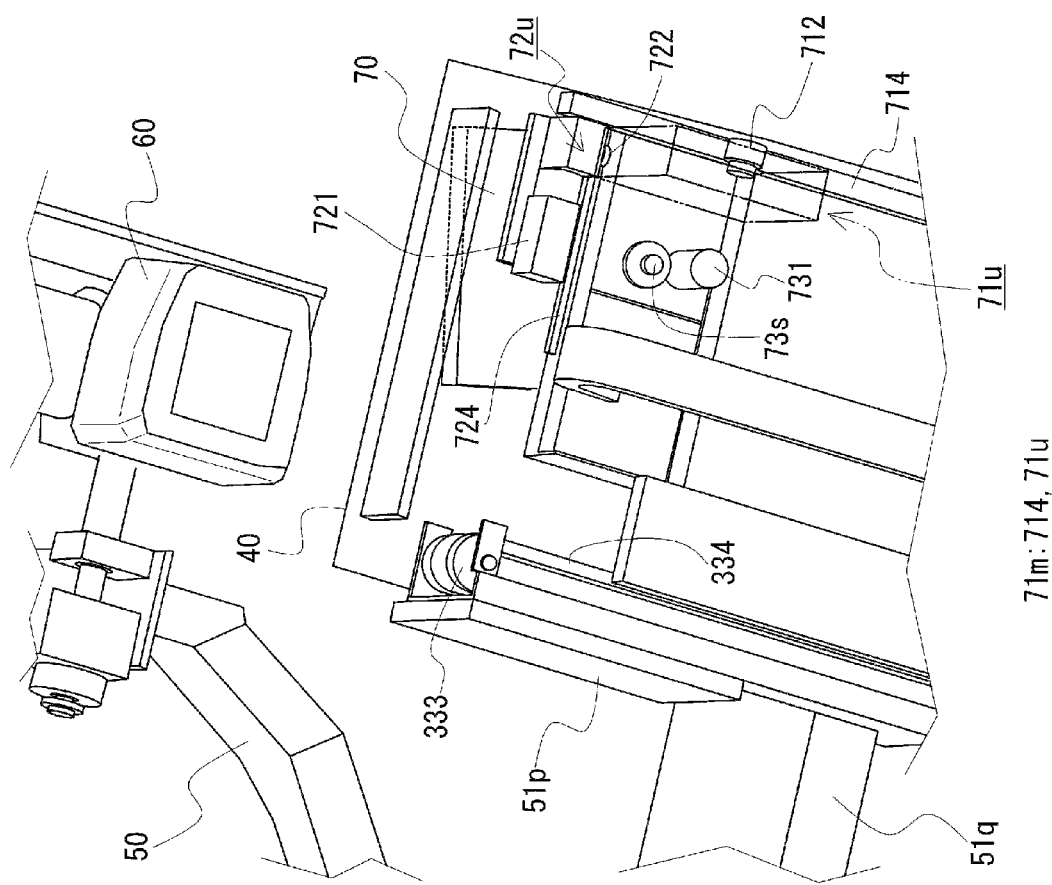
FIG. 10 is a perspective view of the X-ray fluoroscope table from which the cover for covering the respective parts of the table is removed, viewing obliquely from the bottom thereof for showing the mechanism to operate the FPD in the width direction of the support frame and the rotational operation mechanism of the FPD.

The FPD driving mechanism 70m in which the FPD 70 is disposed comprises A7-direction sliding mechanism 71m for sliding the FPD 70 in the longitudinal direction of the support frame 30 with respect to the support frame 30 and A8-direction sliding mechanism 72m for sliding the FPD 70 in the width direction of the support frame 30 with respect to the support frame 30 (refer to FIG. 9 and FIG. 10).

The A7-direction sliding mechanism 71m is fixed to the support frame 30, and is formed by rack 714 extended in the longitudinal direction of the support frame 30 and A7-direction sliding unit 71u which moves along the rack 714. The A7-direction sliding unit 71u has motor 711 and pinion 712 to be rotated by the drive of the motor 711. The pinion 712 of the sliding unit 71u is interlocked with the rack 714 of the support frame 30, thus can move the sliding unit 71u along the rack 714 by rotating the pinion 712.

To the A7-direction sliding unit 71u, rack 724 which is extended in the width direction of the support frame 30 is fixed. Also, on the upper part of the A7-direction sliding unit 71u, A8-direction sliding unit 72u comprising pinion 722 interlocked with the rack 724 and first motor 721 for rotating the pinion 722 is provided. Thus by rotating the pinion 722 of the A8-direction sliding unit 72u, the sliding unit 72u can be moved along the rack 724 of the A7-direction sliding unit 71u.

Furthermore, the A8-direction sliding unit 72u comprises rotation axis unit 73s to be coupled to the FPD 70 and second motor 731 for rotating the rotation axis unit 73s. Thus by rotating the rotation axis unit 73s, the FPD 70 can be rotated (arrow A9-direction in FIG. 2). The rotation axis unit 73s can rotate the FPD 70 by 90 degrees. Therefore, the rotation mechanism comprising the rotation axis unit 73s and the second motor 731 is configured to change the horizontal and vertical directions of the FPD 70.

[Display Device]

The display device 80 is formed by two-pieces of monitors 81 and 82 disposed in parallel, and is supported by the stand unit 10 via multi-joint arm 800 as shown in FIG. 2. The fluoroscope images of the object P can be displayed on the monitors 81 and 82. Also, from among the two pieces of monitors 81 and 82, one can be used for displaying the images inputted from the equipment other than the imaging table 1. For example, endoscopic images or ultrasonic diagnostic images may be displayed.

The multi-joint arm 800 for supporting the monitors 81 and 80 are formed by first arm 801 by which one end is rotatably and pivotally supported with respect to the stand unit 10, bending arm 802 rotatably and pivotally supported with respect to the end of the first arm 801, and connecting portion 803 for connecting the bending arm 802 and the monitors 81 and 82. The monitors 81 and 82 are rotatably connected centering around the connecting portion 803 such that they can be moved in the direction that operators can observe them easily. Also, the two pieces of monitors 81 and 82 can be respectively pointed in different directions.

[Pressing Device]

Figure 5:
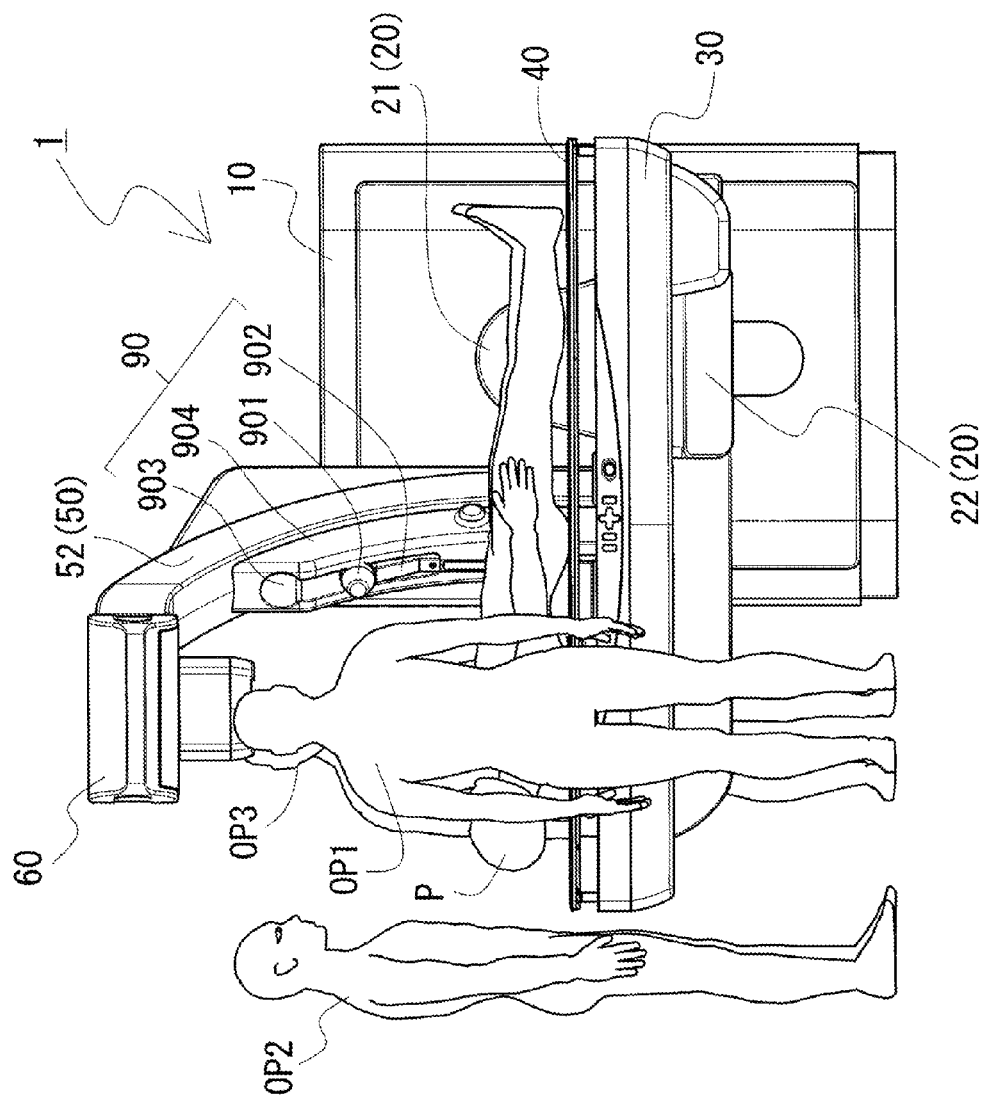
FIG. 5 is a side view illustrating the state wherein the object and the operators are placed at the X-ray fluoroscope table.

The pressing device 90 comprises pressing tube 901, pulling arm 902 and cover 904 having storage unit 903 for containing them as shown in FIG. 5. The pressing tube 901 is a truncated cone-shaped member capable of pressing the region of interest of the object P. The pulling arm 903 is for holding the pressing tube 901 onto the column unit 50, and pulling the pressing tube 901 toward the object P. The pulling arm 902 may have configuration in which a plurality of rod-like members are folded or nested. It should be noted however that the pulling arm 902 needs to be configured so that when the pressing tube 901 is pulled toward the object P side, the central axis of the pressing tube 901 matches the optical axis of X-rays. The pressing tube 901 and the pulling arm 902 can be contained in storage unit 903 of the cover 904 when not in use. As for the storage condition, there are conditions that the whole pulling arm 902 and a part of the pressing tube 901 is contained (FIG. 5) and the condition that both of them are completely contained (FIG. 2).

[Fluoroscope Imaging Using the X-Ray Fluoroscope System]

The state of fluoroscope imaging using the X-ray fluoroscope system and the above-described X-ray fluoroscope table will be described based on FIG. 11. In FIG. 11, only the fluoroscope table of the fluoroscope system will be illustrated. Also, the dashed line in FIG. 11 indicates the movement range of the FPD 70.

First, in the case of imaging in the vicinity of the head region of the object P using the system, as shown in FIG. 11(A), the operators can have access to the object P from three directions which are the head-region side of the object P and both sides of the support frame 30 having the X-ray generator 60 therebetween, without moving the respective components of the imaging table 1. Naturally, as shown in FIG. 11(B), the arrangement of the equipment can be that the support frame 30 is moved to the left side on the diagram with respect to the support arm unit 20. In this case, since the stand unit 10 is not placed behind the operator OP3 who stands by the column unit 50, an assistant can stand behind the operator OP3 or surgical tools for the operator OP3 to use can be placed there.

Also depending on the operative procedure of the IVR, there are cases that the region for X-ray irradiation is moved from the chest area to the abdominal area of the object P. With that, FIG. 12(A) shows the condition that the range for X-ray irradiation is moved from the condition in FIG. 11(A) or (B) to the abdominal area of the object P. When the irradiation range is to be moved from the condition of FIG. 11(A) to the condition of FIG. 12(A), the support frame 30 is to be moved to the left side on the diagram with respect to the support arm unit 20, and the column unit 50 is to be moved to the right side on the diagram with respect to the support frame 30. On the other hand, when the irradiation range is to be moved from the condition of FIG. 11(B) to the condition of FIG. 12(A), the column unit 50 is to be moved to the right side on the diagram with respect to the support frame 30 without moving the column unit 30 with respect to the support arm unit 20. Also in the case of FIG. 12(A), the standing position for the operators OP1 and OP3 can be ensured on both sides of the object P having the X-ray generator 60 therebetween, which is appropriate to be applied to the IVR.

In the case that the top board 40 is configured slidably with respect to the support frame 30, the region for the X-ray irradiation can be moved from the chest area toward lower abdomen also by moving the top board 40 in the longitudinal direction with respect to the support frame 30. For example, moving the top board 40 from the condition of FIG. 11(A) in the direction to the left on the diagram with respect to the support frame 30 leads to the condition in FIG. 12(B). However, bending stress acts on the part of the top board 40 which is protruded from the support 30 upon moving the top board 40 with respect to the support frame 30, thus the range for moving the top board 40 in the longitudinal direction with respect to the support frame 30 can not be made too large. Therefore, the range for X-ray irradiation can be moved only from the chest area to the solar plexus area of the object P. Naturally, it is possible to move the range for X-ray irradiation to the lower abdomen by moving the column unit 50 from the condition in FIG. 12(B) further in the right direction on the diagram with respect to the support frame 30. In that case, while the operator OP1 can move to the right side on the diagram in accordance with the range for X-ray irradiation, the operator OP 3 cannot stand in the position facing the operator OP1 having the range of X-ray irradiation therebetween being interfered by the support arm unit 20.

On the other hand, when the support frame 30 is moved with respect to the support arm unit 20 as shown in FIG. 12(A), compared with moving the top board 40 with respect to the support frame 30, the range of X-ray irradiation can be moved to the lower abdomen of the object P as described above. This is because the support frame 30 is firmly held by the support arm unit 20, and can be moved largely in the longitudinal direction of the support frame 30 with respect to the support arm unit 20. This means that, when the region of X-ray irradiation is to be moved from the condition of FIG. 11(A) to the lower abdomen of the object P, the moving distance, i.e. the stroke of the irradiation region can be made longer by moving the support frame 30 with respect to the support arm unit 20 rather than moving the top board 40 with respect to the support frame 30.

[Variety of Operative Procedures to which the X-ray Fluoroscope System of the Present Invention is Applied]

The examples of various operative procedure to which the X-ray fluoroscope system of the present invention is applied will be described based on FIGS. 13~19. In these diagrams, only the X-ray fluoroscope imaging table of the X-ray fluoroscope system will be illustrated.

Figure 13:
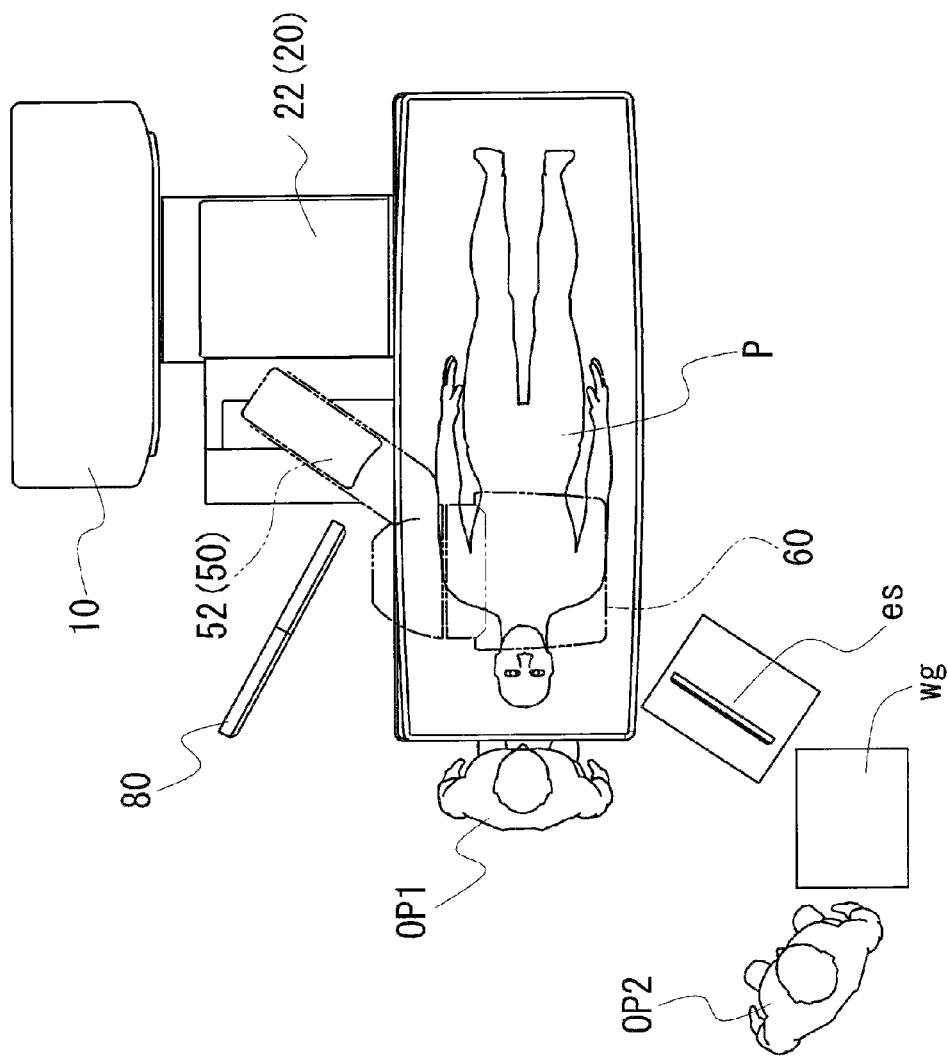
FIG. 13 shows the state wherein the X-ray fluoroscope system of the present invention is applied to a lung biopsy.

FIG. 13 shows the condition wherein the X-ray fluoroscope system of the present invention is applied to a lung biopsy. In FIG. 13, the object P is accessed by the operator OP1 from his/her head region side and the fluoroscope imaging is being performed while the operator OP1 is observing the images of endoscope "es". By moving the display device 80, the object P can be accessed from the side of column unit 50, or the operator OP2 or wagon "wg" can be positioned by the column unit 50.

Figure 14:
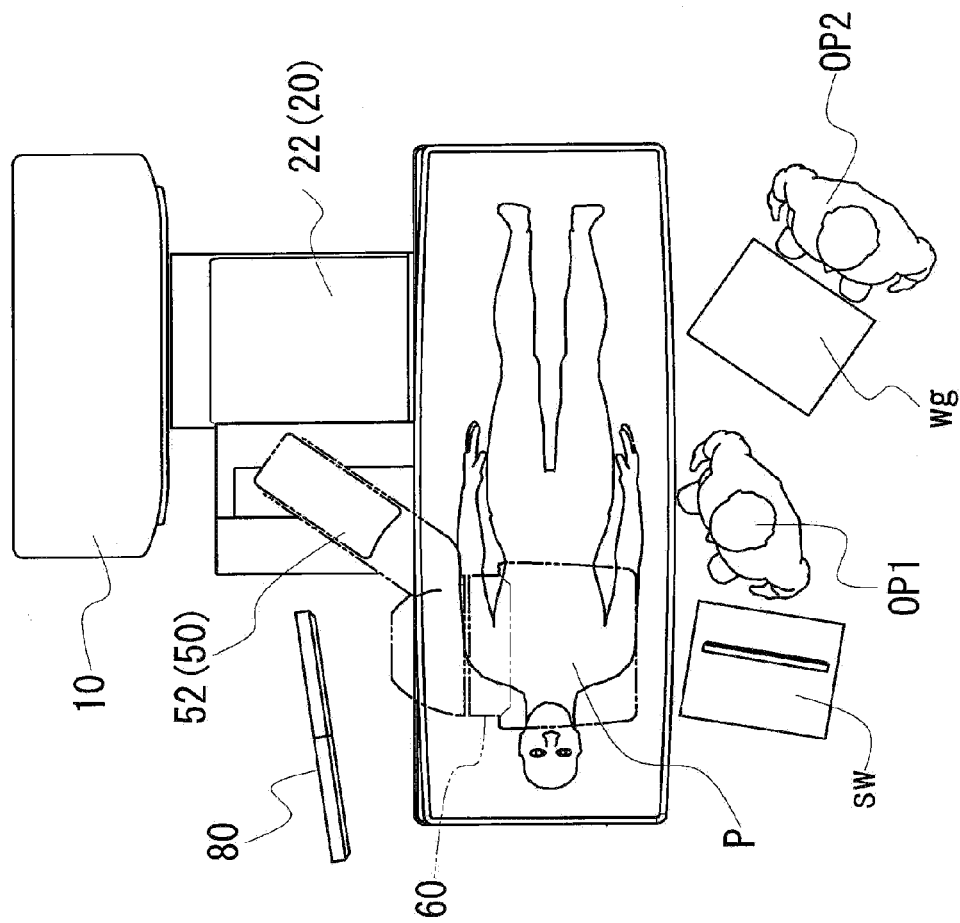
FIG. 14 shows the state wherein the X-ray fluoroscope system of the present invention is applied to an operative procedure of PTCD.

FIG. 14 shows the condition wherein the X-ray fluoroscope system of the present invention is applied to the PTCD (Percutaneous Transhepatic Cholangio Drainage). In FIG. 14, the operator OP1 is accessed from his/her side by the operator OP1, and the fluoroscope imaging is being performed while the operator OP1 is observing the images of ultrasonic diagnostic apparatus "sw". In this case also, by moving the display device 80, the object P can be accessed from the side of column unit 50.

Figure 15:
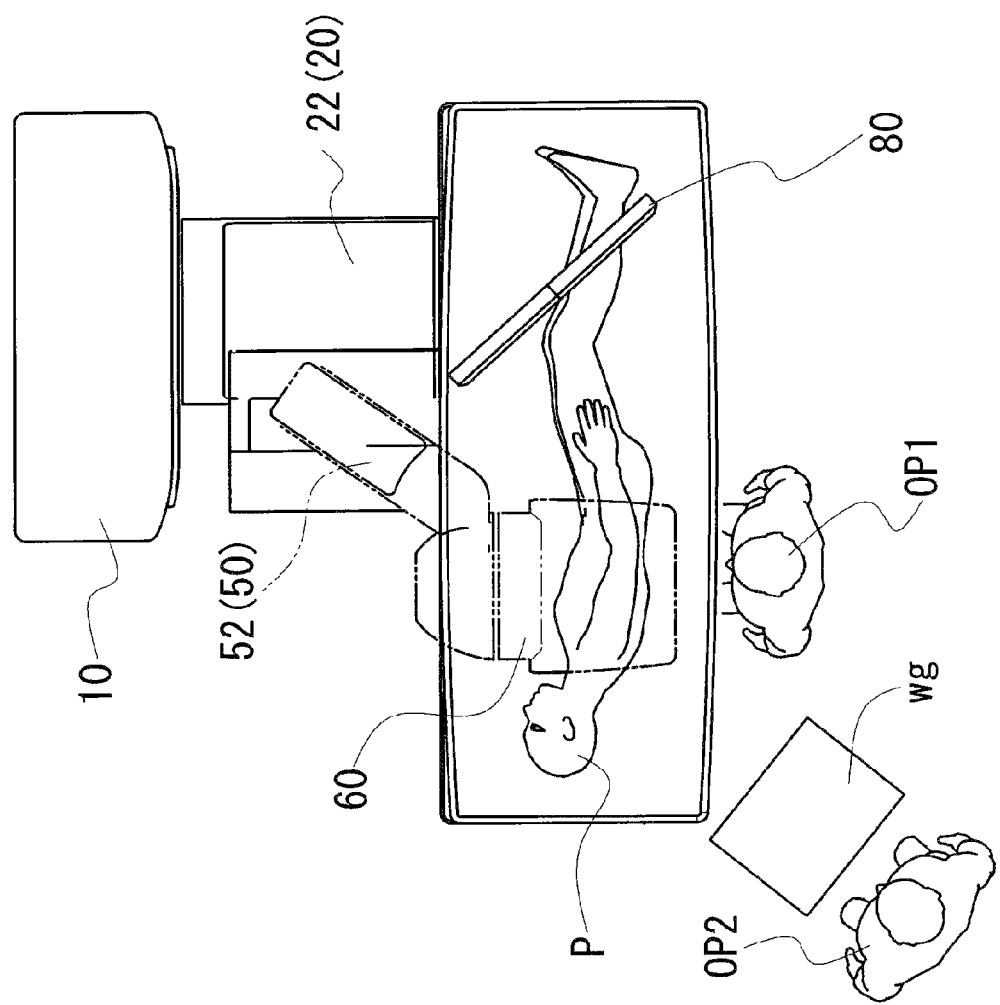
FIG. 15 shows the state wherein the X-ray fluoroscope system of the present invention is applied to a myelography.

FIG. 15 shows the condition wherein the X-ray fluoroscope system of the present invention is applied to a myelography. Also, the object P can be accessed from the side of the column unit 50.

Figure 16:
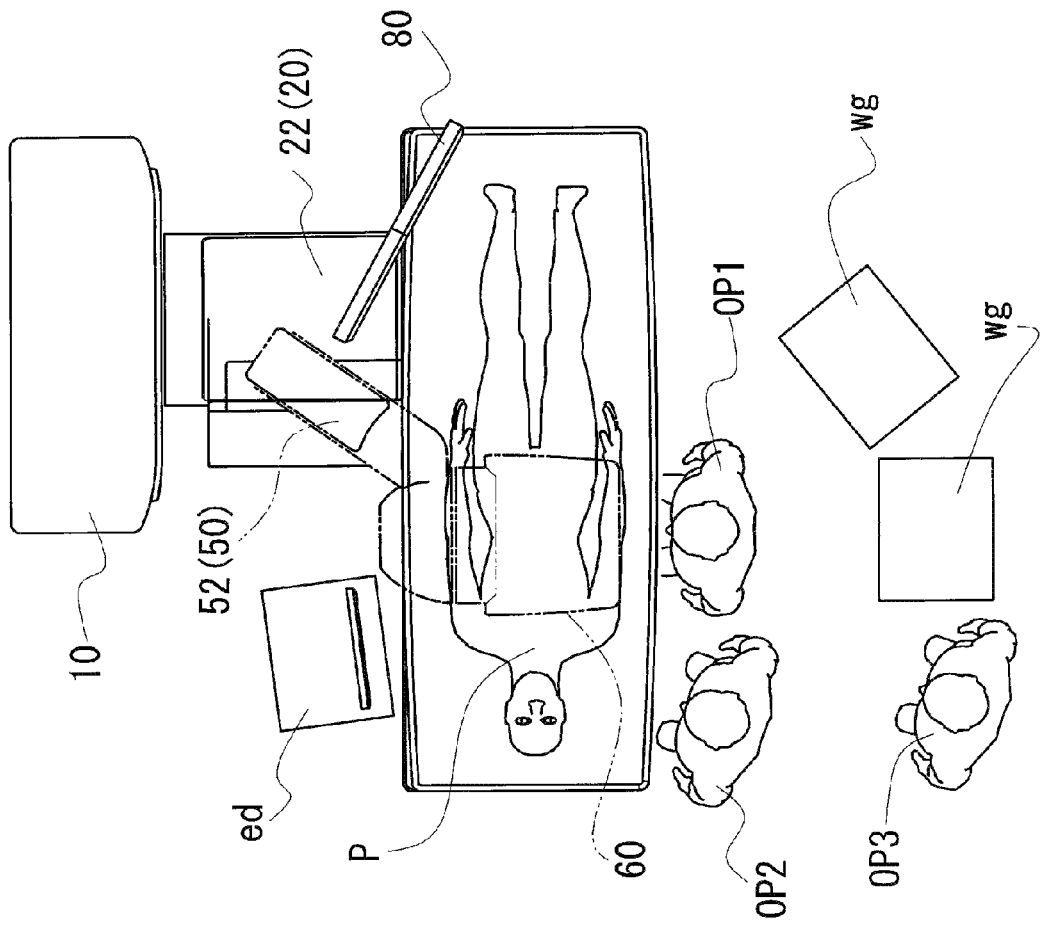
FIG. 16 shows the state wherein the X-ray fluoroscope system of the present invention is applied to an abdominal angiography.

FIG. 16 shows the condition wherein the X-ray fluoroscope system of the present invention is applied to an abdominal angiography. As shown in FIG. 16, an electrocardiograph "ed" can be placed in the vicinity of the column unit 50.

Figure 17:
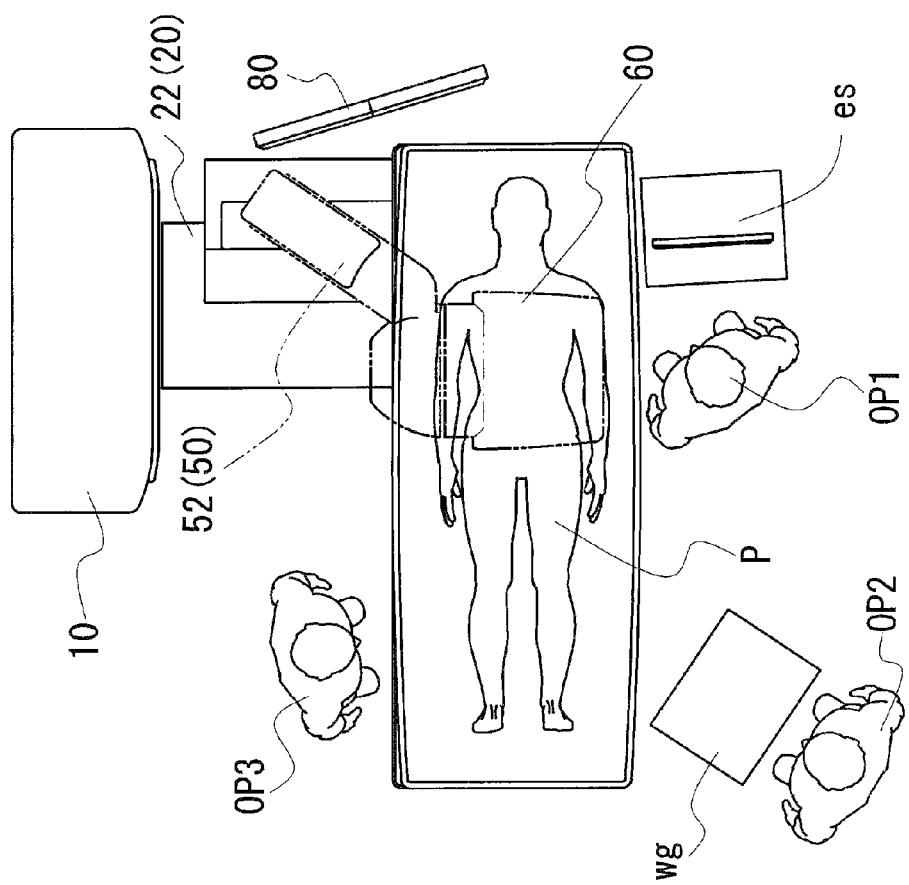
FIG. 17 shows the state wherein the X-ray fluoroscope system of the present invention is applied to an operative procedure of ERPC.

FIG. 17 shows the condition wherein the X-ray fluoroscope system of the present invention is applied to the endoscopic retrograde cholangio-pancreatography. In FIG. 17, the object P is accessed by the operator OP1 from his/her side, and the fluoroscope imaging is being performed while the operator OP1 is observing the endoscopic images. Also, the object P can be accessed from the side of the column unit 50.

Figure 18:
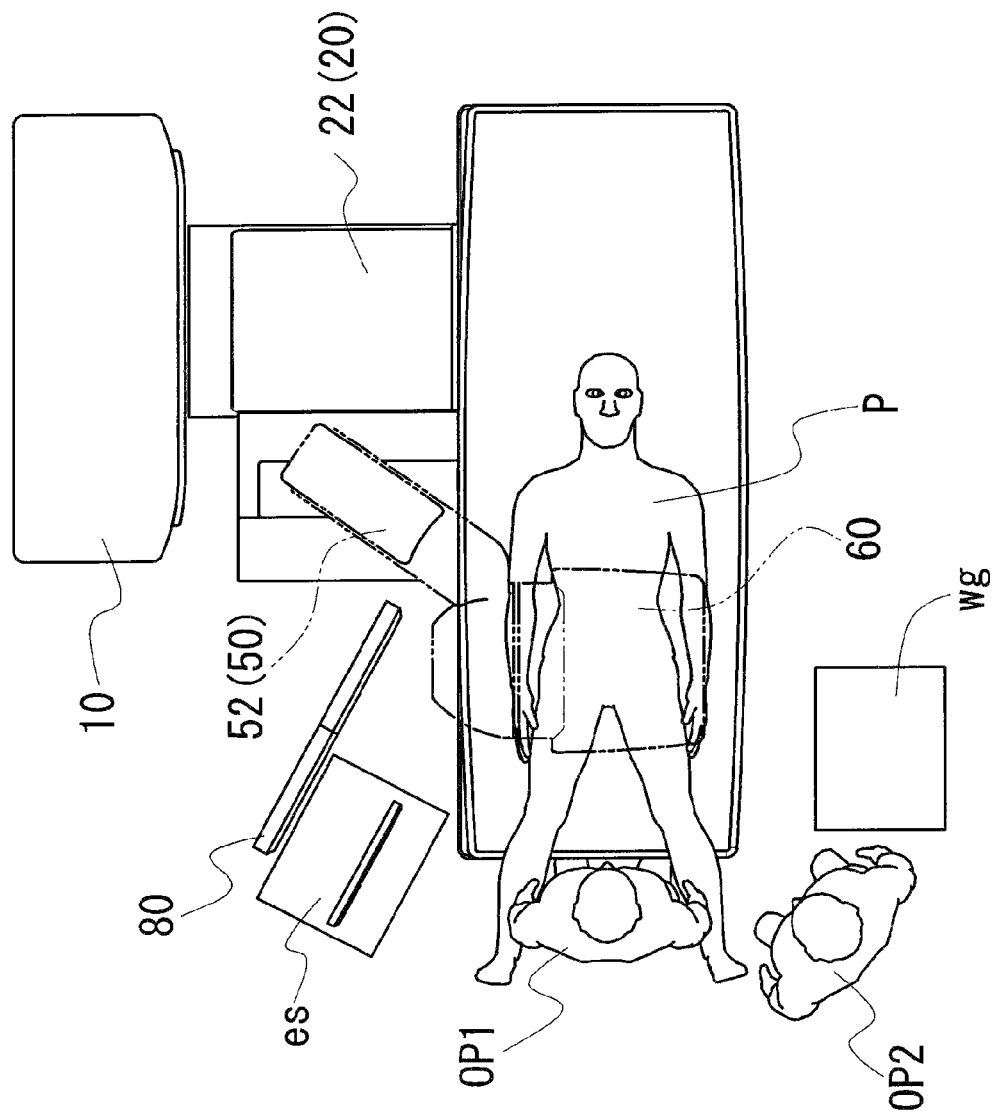
FIG. 18 shows the state wherein the X-ray fluoroscope system of the present invention is applied to a surgery of urinary organs.

FIG. 18 shows the condition wherein the X-ray fluoroscope system of the present invention is applied to a urologic examination. In FIG. 18, the object P is accessed from his/her lower abdominal side by the operator OP1, and the fluoroscope imaging is being performed while the operator OP1 is observing the endoscopic images. Also, the object P can be accessed from the side of the column unit 50.

Figure 19:
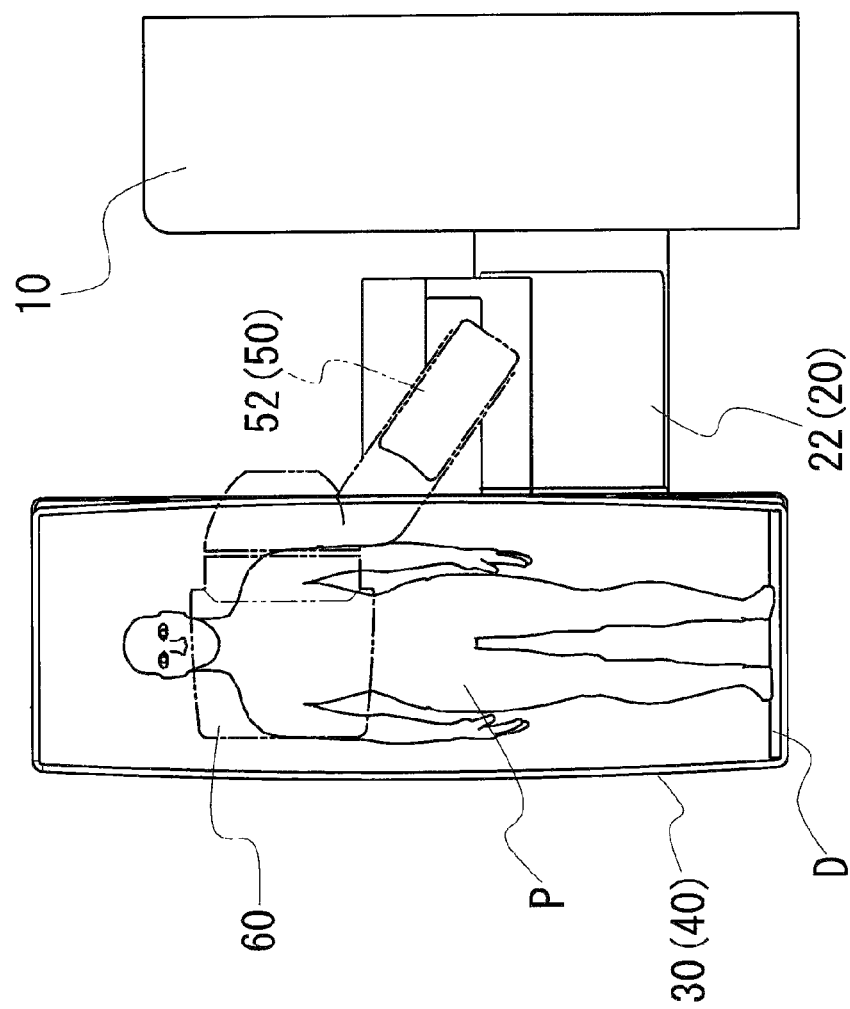
FIG. 19 shows the state wherein the X-ray fluoroscope system of the present invention is applied to a physical check.

FIG. 19 shows the condition wherein the X-ray fluoroscope system of the present invention is applied to a physical examination. In FIG. 18, the imaging is performed while the top board 40 and the support frame 30 are being erected. In this case, the imaging is to be performed in the condition that the object P stands on platform "D" mounted on the lower end of the support frame 30, with the top board 40 on his/her back.

As described above, the X-ray fluoroscope system of the present invention can be used for various purposes, from a variety of IVR procedures to a physical examination. Furthermore, in IVR procedure, since a plurality of operators can have access to the object P from both sides of the object P, the IVR procedure can be carried out effectively. Also, since a number of operators can work on the procedure, it is possible to perform a difficult surgery in a short period of time, whereby reducing the burden of the object P.

INDUSTRIAL APPLICABILITY

The X-ray fluoroscope system comprising the X-ray fluoroscope table of the present invention can be applied to perform IVR procedure effectively.

The invention claimed is:

1. An X-ray fluoroscope table comprising:
   a stand unit installed on a floor;
   a support arm unit supported by the stand unit, and is protruded toward one side of the side surfaces of the stand unit;
   a support frame supported by the support arm unit, and is extended in the direction approximately orthogonal to the protruded direction of the support arm unit;
   a top board supported by the support frame, to which an object is placed;
   an X-ray generator for irradiating X-rays to the object;
   a column unit supported by the support frame, for supporting the X-ray generator, and
   an X-ray detector placed inside of the support frame facing the X-ray generator, for detecting the X-rays transmitted through the object,
   wherein a structure of the column unit is curved to be convex toward the direction away from the support frame, and
   wherein the structure of the column unit is formed to be extended to an area within an angle formed between a longitudinal direction and a width direction of the top board from an end portion of the support frame side toward an end portion on the X-ray generator side in order to make space for an operator to stand between the column unit and the support frame while facing the X-ray generator.

2. The X-ray fluoroscope table according to claim 1, further comprising a basement for sliding the column unit in the longitudinal direction or the width direction of the support frame.

3. The X-ray fluoroscope table according to claim 1, further comprising a rotation mechanism inside of the column unit, for rotating the X-ray generator.

4. The X-ray fluoroscope table according to claim 1, further comprising a sliding mechanism for sliding the X-ray detector in the longitudinal direction or the width direction of the support frame.

5. The X-ray fluoroscope table according to claim 1, further comprising a rotation mechanism for rotating the X-ray detector.

6. The X-ray fluoroscope table according to claim 4, further comprising a sensor for detecting the sliding condition of the column unit, wherein the sliding mechanism causes the X-ray detector to slide by following the movement of the X-ray generator.

7. The X-ray fluoroscope table according to claim 1, further comprising a display device for displaying fluoroscope images of the object, wherein the display device is supported by the stand unit via a multi-joint arm.

8. The X-ray fluoroscope table according to claim 1, further comprising:
   a pressing tube for pressing the object in a region of interest while imaging the object; and
   a pulling arm wherein one end is coupled to the pressing tube and the other end is coupled to the column unit,
   wherein it is configured so that the pressing tube is to be pulled toward a region of interest by the pulling arm when the region of interest is to be pressed by the pressing tube, and the pulling arm is to be stored in the column unit when the region of interest is not to be pressed by the pressing tube.

9. An X-ray fluoroscope system comprising:

an X-ray fluoroscope table according to claim 1 which is to be installed in an imaging room;

a high voltage generator to be installed in the imaging room, for supplying electric power to the X-ray generator; and a remote console to be installed in an operating room which is separate from the imaging room, for integrally controlling the X-ray fluoroscope table and the high-voltage generator.

* * * * *